United States Patent

Witschger et al.

(10) Patent No.: US 6,833,479 B2
(45) Date of Patent: Dec. 21, 2004

(54) ANTIMISTING AGENTS

(75) Inventors: Mark Witschger, Cincinnati, OH (US); Jianhua Mao, West Chester, OH (US); Phillip L. Mattison, Columbia Height, MN (US); Michael J. Virnig, Tucson, AZ (US); Marie-Esther Saint Victor, Cincinnati, OH (US)

(73) Assignee: Cognis Corporation, Ambler, PA (US)

( * ) Notice: Subject to any disclaimer, the term of this patent is extended or adjusted under 35 U.S.C. 154(b) by 0 days.

(21) Appl. No.: 10/618,935

(22) Filed: Jul. 14, 2003

(65) Prior Publication Data

US 2004/0083855 A1 May 6, 2004

Related U.S. Application Data

(60) Provisional application No. 60/404,201, filed on Aug. 16, 2002.

(51) Int. Cl.⁷ ............ C07C 213/00; C25D 21/11; C25C 1/12
(52) U.S. Cl. ............ 564/505; 205/94; 205/585
(58) Field of Search ............ 564/505; 205/94, 205/585

(56) References Cited

U.S. PATENT DOCUMENTS 5,468,353 A  * 11/1995 Anich et al. ............... 205/581
6,599,414 B1 * 7/2003 Virnig et al. ............... 205/581

\* cited by examiner

*Primary Examiner*—Melvyn Andrews
(74) *Attorney, Agent, or Firm*—Aaron R. Ettelman

(57) ABSTRACT

Alkoxylated compounds of formula I $$R((AO)_nH)_mH_p \qquad (I)$$

wherein each AO group is independently an alkyleneoxy group selected from ethyleneoxy, 1,2-propyleneoxy, 1,2-butyleneoxy, and styryleneoxy groups; n is an integer of from 2 to 100; m is an integer of from 1 to the total number of —OH plus —NH hydrogens in the R group prior to alkoxylation; the sum of m plus p equals the number of —OH plus —NH hydrogens in the R group prior to alkoxylation; and the R group is a group selected from the following:

$$N(CH_2CH_2O)_3 \qquad (II);$$

$$R^1N(CH_2CH_2O)_2 \text{ where } R^1 \text{ is a } C_1\text{–}C_{24} \text{ alkyl, aryl, or aralkyl group} \qquad (III);$$

$$R^1N^+(CH_2CH_2O)_3Y^- \text{ where } R^1 \text{ has the above meaning and} \qquad (IV)$$

$Y^-$ is an anion, preferably an inorganic anion such as a halogen anion, a hydrogen sulfate anion, one-half of a sulfate anion, or one-third of a phosphate ion;

$$NCH_2CH_2N \qquad (V);$$

$$NCH_2CH_2NCH_2CH_2N \qquad (VI);$$

$$CH_3C(CH_2O)_3 \qquad (VII);$$

$$CH_3CH_2C(CH_2O)_3 \qquad (VIII);$$

$$C(CH_2O)_4 \qquad (IX); \text{ and}$$

(X)

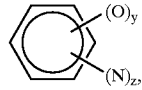

where y is an integer of from 0 to 3, z is an integer of from 0 to 3, provided that the sum of y plus z is 2 or 3; and their use as anti-misting agents.

51 Claims, No Drawings

ANTIMISTING AGENTS

CROSS REFERENCE TO RELATED APPLICATIONS

This application claims the benefit of provisional application Ser. No. 60/404,201, filed on Aug. 16, 2002 now abandoned.

FIELD OF THE INVENTION

This invention relates to the control of mist formation during processes for the electrowinning, electroplating, and electroforming of metals from electrolyte solutions.

BACKGROUND OF THE INVENTION

In the production of metals by electrolysis of aqueous solutions, the electrowinning of the metals is usually carried out in tank cells. Developments in the electrowinning of metals from aqueous solutions have been directed toward improved demisting agents, improved anodes, improved additives, higher current densities, the use of ion-exchange membranes, better electrolyte quality control, and computer modeling of the processes.

Electroplating is the process of applying a metallic coating to an article by passing an electric current through an electrolyte in contact with an article. The ASTM adds some quality restriction by defining electroplating as electrodeposition of an adherent metallic coating on an electrode such that a surface having properties or dimensions different from those of the basic metal is formed.

Progress in electroplating is linked to improvements in materials of construction, power supplies and other plating equipment, purer industrial chemicals and anodes, improved additives such as demisting agents for the plating baths, and improved analytical test and control methods. The quality of electroplating is dependent on the basic metal surface. Cleaner, less porous castings and better casing alloys, and improved steel and steel finishes have helped significantly.

Electroforming involves the electrodeposition upon a mandrel or mold in which the separated electrodeposit is the manufactured article.

A problem common to all of the above electrolysis procedures is the presence of mist generated above the electrolyte solutions. In order to reduce the quantity of mist, antimisting (also referred to as demisting and mist-suppressing) agents are commonly added to the electrolyte solutions. However, the currently available antimisting agents are not completely satisfactory, due to limited demisting ability, high loss rate, interference with the electrolysis procedure, and/or ecological incompatibilities.

SUMMARY OF THE INVENTION

This invention relates to antimisting agents for the control of mist generated above electrolyte solutions during the electrowinning, electroplating, and electroforming of metals present in the electrolyte solutions.

The antimisting agents of the invention are alkoxylated compounds having the following structure:

$$R((AO)_nH)_mH_p \qquad (I)$$

wherein each AO group is independently an alkyleneoxy group selected from ethyleneoxy, 1,2-propyleneoxy, 1,2-butyleneoxy, and styryleneoxy groups; n is an integer of from 2 to 100; m is an integer of from 1 to the total number of —OH plus —NH hydrogens in the R group prior to alkoxylation; the sum of m plus p equals the number of —OH plus —NH hydrogens in the R group prior to alkoxylation; and the R group is a group selected from the following:

$$N(CH_2CH_2O)_3 \qquad (II);$$

$R^1N(CH_2CH_2O)_2$ where $R^1$ is a $C_1$–$C_{24}$ alkyl, aryl, or aralkyl group (III);

$R^1N^+(CH_2CH_2O)_3Y^-$ where $R^1$ has the above meaning and (IV)

$Y^-$ is an anion, preferably an inorganic anion such as a halogen anion, a hydrogen sulfate anion, one-half of a sulfate anion, or one-third of a phosphate ion;

$$NCH_2CH_2N \qquad (V);$$

$$NCH_2CH_2NCH_2CH_2N \qquad (VI);$$

$$CH_3C(CH_2O)_3 \qquad (VII);$$

$$CH_3CH_2C(CH_2O)_3 \qquad (VIII);$$

$$C(CH_2O)_4 \qquad (IX); \text{ and}$$

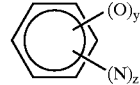
(X)

where y is an integer of from 0 to 3, z is an integer of from 0 to 3, provided that the sum of y plus z is 2 or 3.

The invention also relates to a method for controlling misting in electrolyte solutions of metal ions by adding thereto a mist suppressing quantity of at least one of the above demisting agents.

DETAILED DESCRIPTION OF THE INVENTION

Other than in the operating examples, or where otherwise indicated, all numbers expressing quantities of ingredients or reaction conditions used herein are to be understood as modified in all instances by the term "about".

In the alkoxylated compounds of formula I, the total number of alkyleneoxy groups present therein is preferably from 2 to 50, and more preferably from 2 to 30. Compounds that contain ethylenenoxy groups plus propylenenoxy, butyleneoxy, and/or styryleneoxy groups are highly preferred, especially those that contain from 2 to 25 ethyleneoxy groups and from 2 to 15 propyleneoxy, butyleneoxy, and/or styryleneoxy groups. The styryleneoxy groups can be unsubstituted, or can contain substituents on the phenyl group such as one or more $C_1$–$C_6$ alkyl groups, $C_1$–$C_6$ alkoxy groups and other groups that will not interfere with electrolysis. Also, compounds that are fully alkoxylated are preferred, i.e. compounds of formula I in which p=0.

Also, compounds wherein the R group is the formula II group, i.e. alkoxylated triethanolamine compounds are preferred for use herein especially those which contain from 6 to 15 ethyleneoxy groups, and from 6 to 15 propyleneoxy groups. Such compounds include, but are not limited to, the following; in which POP stands for polyoxypropylene and POE stands for polyoxyethylene, and the numbers following each POP and POE designation mean the number of each groups present in the compound; wherein the POE groups are positioned between the triethanolamine and the POP groups.

POP(6) POE(9)triethanolamine
POP(9) POE(9)triethanolamine
POP(12) POE(9)triethanolamine
POP(15) POE(9)triethanolamine
POP(6) POE(15)triethanolamine
POP(9) POE(15)triethanolamine
POP(12) POE(15)triethanolamine
POP(15) POE(15)triethanolamine
POP(3) POE(6)triethanolamine
POP(6) POE(6)triethanolamine
POP(9) POE (6)triethanolamine
POP(12) POE (6)triethanolamine In the compounds of formula I in which the R group has the formula III, i.e. alkoxylated N-alkyl-diethanolamines, compounds in which the $R^1$ group contains from 1 to 18 carbon atoms are preferred. Also, compounds containing from 2 to 20 ethyleneoxy groups and from 2 to 15 propyleneoxy, butyleneoxy, and/or styryleneoxy groups are preferred.

In compounds of formula I in which the R group has the formula IV, i.e. alkoxylated N-alkyl-triethanolamonium salts, compounds in which the $R^1$ group contains from 1 to 20 carbon atoms are preferred. Also, compounds containing from 2 to 40, preferably from 3 to 25, ethyleneoxy groups, and from 2 to 20, preferably from 2 to 16, propyleneoxy, butyleneoxy and/or styryleneoxy groups are also preferred.

In the compounds of formula I in which the R group has the formula V, i.e. alkoxylated ethylenediamines, compounds containing from 2 to 40, preferably from 4 to 20, ethyleneoxy groups, and from 2 to 20, preferably 4 to 16 propyleneoxy, butyleneoxy, and/or styryleneoxy groups are preferred.

In the compounds of formula I in which the R group has the formula VI, i.e. alkoxylated diethylenetriamines, compounds containing from 2 to 60, preferably from 4 to 30, ethyleneoxy groups, and from 3 to 40, preferably 3 to 20 propyleneoxy, butyleneoxy, and/or styryleneoxy groups are preferred.

In the compounds of formula I in which the R group has the formula VII or VIII, i.e. alkoxylated trimethylol-ethane or -propane, compounds containing from 3 to 60, preferably from 4 to 40, ethyleneoxy groups, and from 3 to 40, preferably 4 to 30 propyleneoxy, butyleneoxy, and/or styryleneoxy groups are preferred.

In the compounds of formula I in which the R group has the formula IX, i.e. alkoxylated pentaerythritols, compounds containing from 4 to 60, preferably from 4 to 40, ethyleneoxy groups, and from 2 to 40, preferably 4 to 20 propyleneoxy, butyleneoxy, and/or styryleneoxy groups are preferred.

In the compounds of formula I in which the R group has the formula X, e.g. alkoxylated phenylenediamine, compounds containing from 4 to 60, preferably from 4 to 40, ethyleneoxy groups, and from 4 to 40, preferably 4 to 30 propyleneoxy, butyleneoxy, and/or styryleneoxy groups are preferred.

In all of the above compounds of formula I, in addition to the ethyleneoxy groups, propyleneoxy, butyleneoxy, and/or styryleneoxy groups should generally also be present, and should be present in a quantity that will balance the hydrophilic and lipophilic properties of the compounds.

As stated above, the $R^1$ group in formulas III and IV are $C_1$–$C_{24}$ alkyl, aryl, or aralkyl groups. The alkyl groups can be straight or branched chain groups, and can be unsubstituted or substituted with one or more $C_1$–$C_6$ alkoxy groups, or other groups that will not interfere with the electrolysis of metals. When the $R^1$ group is an aryl group, the aryl groups can be a substituted or unsubstituted phenyl, naphthyl, or aryl group containing more than two rings. The substituents can include one or more $C_1$–$C_6$ alkyl and/or $C_1$–$C_6$ alkoxy groups. The aralkyl groups can include an aryl group such as the above, attached to a $C_1$–$C_{18}$ alkylene group.

Also, highly preferred compounds of formula I are those in which the AO groups are present in blocks and in the order shown below, i.e. compounds of formula IA:

$$R((EO)_w(PO)_x(BO)_y(SO)_zH)_m \qquad (IA)$$

in which EO=ethyleneoxy; PO=propylenenoxy; BO=butyleneoxy; SO=styryleneoxy; w=2 to 60; x, y, and z each independently=0 to 40; provided that the total of w, x, y, and z does not exceed 100; and further provided that x, y, and z are not all 0.

The above compounds can be readily manufactured by alkoxylating the corresponding alcohols and amines by methods well known to those skilled in the art, e.g. by reacting the alcohols and amines with the desired quantities of alkylene oxides.

In the electrolysis of metals from aqueous electrolyte solutions containing the metal or metals to be plated, the present invention is not dependent on the particular metals present in the electrolyte solutions. Also, with respect to electrowinning processes, different extraction processes can be used with respect to the metal ores. For example, nickel ores are typically leached with ammonia, extracted from the ammonia solutions, and stripped with acid to form an aqueous acidic electrolyte solution used in the electrowinning step. In the electrowinning of aqueous acidic electrolyte solutions containing zinc ions, it is not necessary to carry out the SX process described below for copper to preconcentrate the metal ions for electrowinning.

The solvent extraction process (SX process) for extracting metals such as copper typically involves the following steps, which result in electrolyte solutions in the electrowinning process for the recovery of copper metal. Other processes can be employed with other metals such as nickel, zinc and the like to produce an electrolyte from which their respective metals are electrowon:

1. Aqueous acid leaching of the copper ore using a strong acid to form an aqueous acid leach solution containing copper ions and often relatively small quantities of other metal ions. The aqueous leach acid solution dissolves salts of copper and other metals if present as it is contacted with the ore, e.g. as it trickles through the ore. The metal values are usually leached with aqueous sulfuric acid, producing a leach solution having a pH of 0.9 to 2.0.

2. The copper-pregnant aqueous acid leach solution is mixed in tanks with an oxime extraction reagent which is dissolved in a water-immiscible organic solvent, e.g., a kerosene or other hydrocarbons. The reagent includes the oxime extractant which selectively forms a metal-extractant complex with the copper ions in preference to ions of other metals. The step of forming the complex is called the extraction or loading stage of the solvent extraction process. The oxime extractants used in this step are oxime extractants of the hydroxyl aryl ketone oxime or hydroxy aryl aldoxime type, or a mixture thereof.

3. The outlet of the mixer tanks continuously feeds to a large settling tank or equivalent equipment, where the organic solvent (organic phase), now containing the copper-extractant complex in solution, is separated from the partially depleted aqueous acid leach solution (aqueous phase). This part of the process is called phase separation. Usually, the process of extraction is repeated through two or more mixer/settler stages, in order to more completely extract the copper.

4. After extraction, the partially depleted aqueous acid leach solution (raffinate) is either recycled for further leaching, or recycled with a bleed, or discharged.

5. The loaded organic phase containing the dissolved copper-extractant complex is fed to another set of mixer tanks, where it is mixed with an aqueous strip solution of more concentrated sulfuric acid. The highly acid strip solution breaks apart the copper-extractant complex and permits the purified copper to pass and concentrate in the strip aqueous phase. The process of breaking the copper-extractant complex is called the stripping stage, and the stripping operation may be repeated through two or more mixer-settler stages to more completely strip the copper from the organic phase.

6. As in the extraction process described above (step 2 and 3), the mixture of stripped organic phase and copper pregnant aqueous acid strip solution is fed to another settler tank for phase separation, or to another type of solvent extraction equipment that replaces the traditional mixer-settler.

7. From the stripping settler tank, the regenerated stripped organic phase is recycled to the extraction mixers to begin extraction again, and the copper is recovered from the strip aqueous phase, customarily by feeding the strip aqueous phase to an electrowinning tankhouse, where the copper metal values are deposited on plates by a process of electrodeposition.

8. After recovering the copper values from the aqueous solution by electrodeposition, the solution, known as spent electrolyte, is returned to the stripping mixers to begin stripping again.

In stage 7 of the above process, acid mist is generated above the electrolyte (strip aqueous phase) during the electrowinning (electrodeposition) process. While the metal is plated at the cathode during the electrowinning process, small bubbles of oxygen are generated at the anode. These bubbles rise to the top of the electrolyte and break, propelling small particles of acidic electrolyte into the air and causing an acidic mist. Thus electrowinning mist usually is corrosive to buildings and equipment, and hazardous to humans.

As discussed above, this misting problem is also present in electroplating and electroforming procedures that utilize aqueous electrolyte solutions of metals ions or aqueous electrolyte dispersions of metals in metallic form. It is understood that the term "metals" also includes metalloids.

In the electrowinning of metals or metalloids, the metals or metalloids can be one or more of zinc, nickel, copper, chromium, manganese, iron, cobalt, gallium, germanium, arsenic, selenium, ruthenium, rhodium, palladium, silver, cadmium, indium, tin, lead, bismuth, mercury, antimony, gold, iridium, and platinum. The above metals or metalloids can be present in the aqueous compositions in metallic form and/or in the form of anions.

In addition to the metals listed above, many alloys are commercially electroplated, such as brass, bronze, many gold alloys, lead-tin, nickel-iron, nickel-cobalt, nickel-phosphorous, tin-nickel, tin-zinc, zinc-nickel, zinc-cobalt, and zinc-iron. Electroplated alloys in lesser use include lead-indium, nickel-manganese, nickel-tungsten, palladium alloys, silver alloys, and zinc-manganese.

Another type of electrodeposit in commercial use is the composite form, in which insoluble materials are codeposited along with the electrodeposited metal or alloy to produce particular desirable properties. Polytetrafluoroethylene (PTFE) particles are codeposited with nickel to improve lubricity. Silicon carbide and other hard particles including diamond are co-deposited with nickel to improve wear properties or to make cutting and grinding tools.

The term "metalloid" is to be understood to mean non-metals which are semiconductors, e.g. arsenic, germanium, and the like, which can be electroplated in the same manner as metals.

The essential components of an electroplating process are an electrode to be plated (the cathode); a second electrode to complete the circuit (the anode); an electrolyte containing the metal ions to be deposited; and a d-c power source. The electrodes are immersed in the electrolyte such that the anode is connected to the positive leg of the power supply and the cathode to the negative. As the current is increased from zero, a minimum point is reached where metal plating begins to take place on the cathode.

There are a number of electroplating methods for which the demisting agents of the invention can be used. Materials such as strip steel can be plated in plating tanks where coils of steel are unrolled in a continuous basis, fed through a series of preparation steps, and then into the plating tank. To electroplate wire, the wire is uncoiled from spools or reels, passed through processing steps and then plated as individual strands. Wire is plated commercially with metals such as copper, copper alloys, zinc, iron, iron alloys, nickel, nickel alloys, gold, and silver. Stampings, moldings, and castings are typically mounted onto specially designed plating racks. Bulk plating methods can be used for small parts, e.g. dipping baskets and plating barrels made of inert plastic materials. Where parts are large and only smaller areas of the parts are to be plated, brush plating is used, i.e. using plating tools which are shaped anode materials covered with an absorbent material saturated with the plating solution.

Plating tanks are formed from materials which are either totally inert to the plating solution or are lined with inert materials to protect the tank. For alkaline plating solutions, mild steel materials are used. For acid plating solutions other materials are used, depending on the chemical composition of the plating bath, such as titanium and various stainless steel alloys, polytetrafluoroethylene, KARBATE®, HASTALLOYS®, zirconium alloys, and the like.

The plating tanks are fitted for d-c power, usually with round copper busbars. Filters are usually present to remove fine particulate matter. Heating or cooling units may be present, such as heating coils or cooling water coils. Two types of anodes can be used, i.e. soluble or insoluble. (See e.g., Kirk-Othmer, Encyclopedia of Chemical Technology, $4^{TH}$ Edition under the heading Electroplating).

Insoluble anodes are used exclusively in the plating baths of the present invention. Chromium plating solutions utilize lead-tin, lead-antimony, or lead anodes. Gold and other precious metal plating processes use stainless steel anodes, keeping inventory costs down.

Whenever insoluble anodes are used, the pH of the plating solution decreases along with the metal ion concentration. In some plating baths, a portion of the anodes is replaced with insoluble anodes in order to prevent metal ion buildup or to reduce metal ion concentration.

The use of insoluble anodes can also result in side effects. In alkaline cyanide solutions, the generation and buildup of carbonates is accelerated, along with a significant reduction in alkalinity. In acid solutions the pH decreases as well, requiring frequent adjustments. In sulfamate nickel plating solution, insoluble anodes, and even slightly passive soluble anodes, partially oxidize the sulfamate ion to form sulfur-bearing compounds which change the character and performance of the deposit. (See Kirk-Othmer, supra).

The substrates being electroplated must usually be prepared prior to electroplating. Because electroplating takes place at the exact molecular surface of a work, it is important that the substrate surface be absolutely clean and receptive to the plating. In the effort to get the substrate into this condition, several separate steps may be required, such as soak cleaning, followed by electrocleaning, followed by rinsing.

Formulations of plating baths can be flexible in some systems and very sensitive to variations in others. Many of the more recent changes have resulted from waste treatment and safety requirements. Besides the ability to deposit a coating having acceptable appearance and physical properties, the desired properties of the plating bath include: high metal solubility, good electrical conductivity, good current efficiencies for anode and cathode, noncorrosivity to substrates, nonfuming, stable, low hazard, low anode dissolution during down-time, good throwing power, good covering power, wide current density plating range, ease of waste treatment, and economical to use. Few formulas have all these attributes. Only a few plating solutions are commercially used without special additives, but chemical costs often constitute a relatively low percentage of the total cost of electroplating. Additives are used to brighten, reduce pitting, or otherwise modify the character of the deposit or performance of the solution. Preferred formulations are normally specified by the suppliers of the proprietary additives.

Purification, often needed once a plating bath is made, is used periodically to maintain the plating solutions. Alkaline zinc plating solutions are sensitive to a few mg/L of heavy-metal contamination, which can be precipitated using sodium sulfide and filtered out. Nickel plating solutions may contain excess iron and unknown organic contaminants. Iron is removed by peroxide oxidation, precipitation at a pH of about 5, and filtered out. The more complex, less water-soluble organic contaminants along with some trace metals are removed with activated carbon treatments in separate treatment tanks.

Another common purification treatment used both on new and used plating solution is dummying. Heavy-metal impurities are removed by electrolyzing, usually at low current densities, using large disposable steel cathodes. Good agitation and lower pH speed the process.

Analysis and testing are required whenever a new plating solution is made up, and thereafter at periodic intervals. The analyses are relatively simple and require little equipment. Trace metal contaminants can be analyzed by using spot tests, calorimetrically, and with atomic absorption spectrophotometry. Additives, chemical balance, impurity effects, and many other variables are tested with small plating cells, such as the Hull cell.

The precise makeup of plating bath compositions depends on the metal being plated. For example, alkaline cadmium plating baths usually contain cyanide salts, such as sodium cyanide, while acidic baths contain an acid, usually sulfuric acid. Various additives may also be present.

Cyanide copper plating baths typically contain copper metal, copper cyanide, potassium cyanide, potassium hydroxide, Rochelle salts, and sodium carbonate. Acid copper plating baths typically contain copper metal, copper sulfate, sulfuric acid, and additives.

Watts nickel plating baths typically contain nickel metal, nickel sulfate, nickel chloride, boric acid, and additives. Sulfamate nickel plating baths contain nickel sulfamate instead of nickel sulfate.

Silver plating baths typically contain silver cyanide, potassium cyanide, potassium carbonate, and sometimes potassium nitrate and potassium hydroxide, plus additives.

Zinc plating baths can range from simple zinc sulfate solutions to zinc plus chloride/boric acid baths with brighteners and wetting agents. Also, zincate baths and cyanide baths are also used.

Electroforming is the production or reproduction of articles by electrodeposition upon a mandrel or mold that is subsequently separated from the deposit. The separated electrodeposit becomes the manufactured article. Of all the metals, copper and nickel are most widely used in electroforming. Mandrels are of two types: permanent or expendable. Permanent mandrels are treated in a variety of ways to passivate the surface so that the deposit has very little or no adhesion to the mandrel, and separation is easily accomplished without damaging the mandrel. Expendable mandrels are used where the shape of the electroform would prohibit removal of the mandrel without damage. Low melting alloys, metals that can be chemically dissolved without attack on the electroform, plastics that can be dissolved in solvents, are typical examples.

Electrowinning is used in the process of recovering metals from ores. While a process for the electrowinning of copper is given above, it should be noted that the aqueous processes for electrowinning of metals from ores have the following common unit operations or steps: (1) the metal in the ore is converted to an acid-soluble form and this may be an oxidizing roast or reduction; (2) ores from step 1 are leached, usually in sulfuric acid; (3) metal solutions from step 2 are purified and in some cases concentrated; (4) purified metal solutions are electrolyzed in cells where the metal is deposited on the cathode; and (5) acid is produced at the anode and recycled to the leaching step 2. Some acid values are lost, usually in the purification step 3. Makeup acid is added in the leaching step 2. In most cases the metal solution from leaching step 2 contains impurities, including other metals. Many of these metals have the characteristics of low hydrogen over-voltage. Codeposition of the impurity metals causes contamination of the desired product and decreases current efficiencies. The removal of impurities before electrolysis is very important. This is especially true in the case of the more reactive metals such as zinc and manganese. These metals have deposition potentials close to the hydrogen evolution potential. The current efficiency of manganese electrowinning is about 60 to 68%. The principal inefficiency is hydrogen evolution.

It is to be understood that the demisting agents of the invention can be used in electroplating compositions, electroforming compositions, electrowinning compositions, and waste solutions containing dissolved metals.

It is also understood that the component metals and metalloids can be present in ionic form and/or in elementary form.

Extensive research has been devoted to reducing the mist during the electrowinning, electroplating, and electroforming processes, especially in electrowinning processes in which aqueous acidic electrolyte solutions of metal ions are typically used in the electrowinning step.

One, and by far the most common, solution is to add an anti-misting agent to reduce the mist. However, as discussed above, the currently available anti-misting agents are not completely satisfactory.

The most commonly used commercial anti-misting agent is a surfactant which contains a fluorocarbon alkyl group connected to an amphoteric group, which is sold by 3M Corporation under the designation FC-1100 Fluorad™ Brand Mist Control Agent.

There is a need for anti-misting agents that are ecologically compatible, are effective even at low concentrations, have a low loss rate, and do not interfere with the kinetics of metal stripping or phase separation times in steps 5 and 6 of the SX process if the anti-misting agent is present during these steps.

The anti-misting agents of the present invention satisfy all of the above requirements. The anti-misting agents of the invention are effective in quantities as low as a few parts per million, based on the electrolyte composition, e.g. from 2 to 100 ppm, preferably from 2 to 30 ppm, and most preferably from 5 to 25 ppm.

The anti-misting agent can be added to the aqueous strip solution used in step 5 of the SX process, or to the metal pregnant aqueous leach solution in step 6, or preferably to the strip aqueous phase in step 7.

The invention will be illustrated but not limited by the following examples. In the following examples, the compounds were prepared by first reacting ethylene oxide with triethanolamine, and then reacting the resulting reaction product with 1,2-propylene oxide.

EXAMPLES

Example 1

Five hundred ml samples of copper electrolyte solution (50 g/l $Cu^{+2}$, 0.2 g/l $Co^{+2}$, 1.5 g/l $Fe^{+3}$, 170 g/l Sulfuric Acid) containing various quantities of POP(6) POE(9)-triethanolamine were placed in a jacketed beaker controlled at 45° C. Mist was generated by passing air through a fine frit (4-8 micron) scintered glass bubbler in the copper electrolyte. The mist was sampled by suctioning air through a sampling tube 1.5 inches above the liquid level; the tube being connected to a water trap. At timed intervals, the water from the trap was titrated with sodium hydroxide to a bromphenol blue endpoint to determine the amount of acid contained therein. The results given below in Table 1 are calculated in terms of millimoles of sulfuric acid captured per hour.

TABLE 1

POP(6) POE(9) Triethanolamine

| Concentration | mmol Sulfuric Acid/hr |
|---|---|
| None | 0.475 |
| 10 ppm | 0.126 |
| 20 ppm | 0.134 |
| 25 ppm | 0.109 |

Example 2

The process of Example 1 was repeated except that the anti-misting agent was POP(6) POE (15) triethanolamine. The results obtained are set forth in Table 2 below:

TABLE 2

POP(6) POE(15) Triethanolamine

| Concentration | mmol Sulfuric Acid/hr |
|---|---|
| None | 0.310 |
| 8 ppm | 0.193 |
| 20 ppm | 0.112 |
| 25 ppm | 0.077 |

Example 3

The process of Example 1 was repeated except that nitrogen was used instead of air for sparging, using a number of anti-misting agents. The anti-misting agents and the results obtained therewith are set forth in Table 3 below. The terms used in the table have the following meanings:

Mist Reduction—the percent reduction of the millimoles of sulfuric acid captured per hour based on the millimoles of sulfuric acid captured per hour for a blank, i.e. no anti-misting agent present.

Loss Rate—the rate at which mist suppression is lost, based on a previously generated curve of mist vs. concentration of anti-misting agent.

QC kinetics—the effect on strip kinetics in step 5 in the SX process for copper described above (30 sec vs. 300 sec) in a standard QC test, based on the difference from a blank, i.e. the electrolyte solution containing no anti-misting agent.

QC Phase Separation—the effect on strip phase separation rate in step 6 in a standard QC test, based on the difference from a blank.

TEA—triethanolamine.

TABLE 3

| ANTI-MISTING AGENT | PPM | MIST REDUCTION | LOSS RATE | QC KINETICS | QC PHASE SEPARATION |
|---|---|---|---|---|---|
| POP(6) POE(6) TEA | 15 | 54% | 25% in 2 hr | — | — |
| POP(6) POE(9) TEA | 20 | 79% | None | −4.3% at 40 ppm | +6 sec at 40 ppm |
| POP(6) POE(15) TEA | 20 | 54% | — | — | — |
| POP(9) POE(6) TEA | 25 | 93% | <25% in 14 hr | −10.7% at 40 ppm | +19 sec at 40 ppm |
| POP(9) POE(9) TEA | 18 | 68% | — | −15.3% at 40 ppm | +42 sec at 40 ppm |
| POP(9) POE(15) TEA | 15 | 51% | — | — | — |
| POP(12) POE(9) TEA | 20 | 79% | — | −23.8% at 40 ppm | +42 sec at 40 ppm |
| POP(12) POE(15) TEA | 25 | 69% | — | — | — |
| POP(15) POE(9) TEA | 15 | 60% | — | — | — |

TABLE 3-continued

| ANTI-MISTING AGENT | PPM | MIST REDUCTION | LOSS RATE | QC KINETICS | QC PHASE SEPARATION |
|---|---|---|---|---|---|
| POP(15) POE(15) TEA | 25 | 71% | Most in 6 hr | −26.6% at 40 ppm | +19 sec in 40 ppm |
| FC-1100 | 20 | 36% | 100% in 5 hr | −1.3% at 40 ppm | 0 sec at 40 ppm |

What is claimed is:

1. An alkoxylated compound having the following formula I:

$$R((AO)_nH)_mH_p \quad (I)$$

wherein each AO group is independently an alkyleneoxy group selected from ethyleneoxy, 1,2-propyleneoxy, 1,2-butyleneoxy, and substituted or unsubstituted styryleneoxy groups; n is an integer of from 2 to 100; m is an integer of from 1 to the total number of —OH plus —NH hydrogens in the R group prior to alkoxylation; the sum of m plus p equals the number of —OH plus —NH hydrogens in the R group prior to alkoxylation; and the R group is a group selected from the following:

$$N(CH_2CH_2O)_3 \quad (II);$$

$$R^1N(CH_2CH_2O)_2 \text{ where } R^1 \text{ is a } C_1\text{-}C_{24} \text{ alkyl, aryl, or aralkyl group} \quad (III);$$

$$R^1N^+(CH_2CH_2O)_3Y^- \text{ where } R^1 \text{ has the above meaning and} \quad (IV)$$

$Y^-$ is an anion;

$$NCH_2CH_2N \quad (V);$$

$$NCH_2CH_2NCH_2CH_2N \quad (VI);$$

$$CH_3C(CH_2O)_3 \quad (VII);$$

$$CH_3CH_2C(CH_2O)_3 \quad (VIII);$$

$$C(CH_2O)_4 \quad (IX); \text{ and}$$

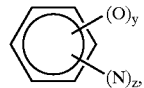
(X)

where y is an integer of from 0 to 3, z is an integer of from 0 to 3, provided that the sum of y plus z is 2 or 3.

2. The alkoxylated compound of claim 1 wherein the compound is an alkoxylated triethanolamine.

3. The alkoxylated compound of claim 1 wherein the compound of formula I contains from 2 to about 50 alkyleneoxy groups.

4. The alkoxylated compound of claim 1 wherein the compound of formula I contains from 2 to about 30 alkyleneoxy groups.

5. The alkoxylated compound of claim 2 wherein the alkoxylated triethanolamine contains from 6 to 15 ethyleneoxy groups and from 6 to 15 propyleneoxy groups.

6. The alkoxylated triethanolamine of claim 2 which is selected from the group consisting of the following:

POP(6) POE(9)triethanolamine
POP(9) POE(9)triethanolamine
POP(12) POE(9)triethanolamine
POP(15) POE(9)triethanolamine
POP(6) POE(15)triethanolamine
POP(9) POE(15)triethanolamine
POP(12) POE(15)triethanolamine
POP(15) POE(15)triethanolamine
POP(3) POE(6)triethanolamine
POP(6) POE(6)triethanolamine
POP(9) POE(6)triethanolamine
POP(12) POE(6)triethanolamine.

7. The alkoxylated compound of claim 1 in which the R group has the formula III.

8. The alkoxylated compound of claim 7 wherein the $R^1$ group contains from 1 to 18 carbon atoms and the compound contains from 2 to 20 ethyleneoxy groups, and from 2 to 15 propyleneoxy, butyleneoxy, and/or styryleneoxy groups.

9. The alkoxylated compound of claim 1 in which the R group has the formula IV.

10. The alkoxylated compound of claim 9 wherein the $R^1$ group contains from 1 to 20 carbon atoms and the compound contains from 2 to 40 ethyleneoxy groups, and from 2 to 20 propyleneoxy, butyleneoxy, and/or styryleneoxy groups.

11. The alkoxylated compound of claim 10 wherein the compound contains from 3 to 25 ethyleneoxy groups, and from 2 to 16 propyleneoxy, butyleneoxy, and/or styryleneoxy groups.

12. The alkoxylated compound of claim 1 wherein the R group has the formula V.

13. The alkoxylated compound of claim 12 wherein the compound contains from 2 to 40 ethyleneoxy groups, and from 2 to 20 propyleneoxy, butyleneoxy, and/or styryleneoxy groups.

14. The alkoxylated compound of claim 13 wherein the compound contains from 4 to 20 ethyleneoxy groups, and from 4 to 16 propyleneoxy, butyleneoxy, and/or styryleneoxy groups.

15. The alkoxylated compound of claim 1 wherein the R group has the formula VI.

16. The alkoxylated compound of claim 15 wherein the compound contains from 2 to 60 ethyleneoxy groups, and from 3 to 40 propyleneoxy, butyleneoxy, and/or styryleneoxy groups.

17. The alkoxylated compound of claim 16 wherein the compound contains from 4 to 30 ethyleneoxy groups, and from 3 to 20 propyleneoxy, butyleneoxy, and/or styryleneoxy groups.

18. The alkoxylated compound of claim 1 wherein the R group has the formula VII or VIII.

19. The alkoxylated compound of claim 18 wherein the compound contains from 3 to 60 ethyleneoxy groups, and from 3 to 40 propyleneoxy, butyleneoxy, and/or styryleneoxy groups.

20. The alkoxylated compound of claim 1 wherein the R group has the formula IX.

21. The alkoxylated compound of claim 20 wherein the compound contains from 4 to 60 ethyleneoxy groups, and from 2 to 40 propyleneoxy, butyleneoxy, and/or styryleneoxy groups.

22. The alkoxylated compound of claim 1 wherein the R group has the formula X.

23. The alkoxylated compound of claim 22 wherein the compound contains from 4 to 60 ethyleneoxy groups, and from 4 to 40 propyleneoxy, butyleneoxy, and/or styryleneoxy groups.

24. The alkoxylated compound of claim 1 wherein the compound has the formula IA below:

$$R((EO)_w(PO)_x(BO)_y(SO)_zH)_m \quad (IA)$$

in which EO=ethyleneoxy; PO=propylenenoxy; BO=butyleneoxy; SO=substituted or unsubstituted styryleneoxy; w=2 to 60; x, y, and z each independently=0 to 40; provided that the total of w, x, y, and z does not exceed 100; and further provided that x, y, and z are not all 0.

25. In an aqueous electrowinning, electroplating, or electroforming electrolyte composition containing at least one metal or metalloid, the improvement wherein the composition contains a mist-suppressing quantity of at least one alkoxylated compound of claim 1.

26. The process of claim 25 wherein said mist-suppressing quantity is in the range of from about 2 to about 100 ppm.

27. The process of claim 26 wherein said quantity is in the range of from about 5 to about 25 ppm.

28. In a solvent extraction process for extracting metals from metal ores using an aqueous leach solution, an extraction reagent dissolved in a water-immiscible organic solvent, an electrolyte solution, and an electrowinning step, the improvement wherein the electrolyte solution contains a mist-suppressing quantity of at least one alkoxylated compound of claim 1.

29. The process of claim 28 wherein said mist-suppressing quantity is in the range of from about 2 to about 100 ppm.

30. The process of claim 29 wherein said quantity is in the range of from about 5 to about 25 ppm.

31. In the electroplating of metals on a substrate from an acidic aqueous electrolyte solution containing metal ions, the improvement wherein the electrolyte solution contains a mist-suppressing quantity of at least one alkoxylated compound of claim 1.

32. In the electrowinning of metals from an acidic aqueous electrolyte solution containing metal ions, the improvement wherein the electrolyte solution contains a mist-suppressing quantity of at least one alkoxylated compound of claim 1.

33. An aqueous electrolyte solution containing:
A) a metal or metalloid in ionic and/or dispersed metallic form; and
B) at least one alkoxylated compound of claim 1.

34. The aqueous electrolyte solution of claim 33 wherein component A) comprises at least one metal selected from the group consisting of copper, cadmium, chromium, cobalt, gold, indium, iron, lead, nickel, a platinum group metal, silver, tin, and zinc.

35. The aqueous electrolyte solution of claim 34 wherein the solution contains from about 2 to about 100 ppm of component B).

36. An aqueous electrolyte solution containing:
A) a metal or metalloid in ionic or dispersed metallic form; and
B) at least one alkoxylated compound of claim 24.

37. A method of suppressing mist in an electrowinning, electroplating, or electroforming process using a metal-containing electrolyte solution comprising adding to the electrolyte solution a mist-suppressing quantity of at least one alkoxylated compound of claim 1.

38. The method of claim 37 wherein the metal in the electrolyte solution is copper ion.

39. The method of claim 37 wherein the at least one alkoxylated compound of claim 1 is an alkoxylated triethanolamine.

40. A method for extracting a metal from a metal-containing ore comprising the steps of
I) contacting the metal-containing ore with an aqueous leach solution to extract metal values therefrom;
II) contacting the aqueous leach solution containing metal values with a water-immiscible organic solvent containing an extraction reagent to obtain a metal-containing organic solvent solution;
III) separating the metal-containing organic solvent solution from the aqueous leach solution;
IV) contacting the metal-containing organic solvent solution with an aqueous acid strip solution;
V) adding to the resulting metal-containing aqueous acid strip solution a mist-supressing quantity of at least one alkoxylated compound of claim 1; and
VI) electrowinning the metal from the aqueous acid strip solution obtained in step V).

41. The method of claim 40 wherein in step II) the extraction reagent is at least one oxime extractant.

42. The method of claim 40 wherein in step V) the mist-suppressing quantity is in the range of from about 2 to about 100 ppm.

43. The method of claim 42 wherein said quantity is in the range of from about 2 to about 30 ppm.

44. The method of claim 42 wherein said quantity is in the range of from about 5 to about 25 ppm.

45. The method of claim 40 wherein the at least one alkoxylated compound of claim 1 is an alkoxylated triethanolamine.

46. A method for extracting copper from a copper-containing ore comprising the steps of
I) forming a copper-pregnant aqueous acid leach solution by contacting a copper-containing ore with an aqueous strong acid to produce a copper-pregnant acid leach solution;
II) contacting the resulting copper-pregnant acid leach solution with an oxime extractant in a water-immiscible organic solvent;
III) separating the resulting copper-pregnant water-immiscible organic solvent from the resulting copper-depleted acid leach solution;
IV) stripping the copper from the copper-pregnant water-immiscible organic solvent with an aqueous acidic strip solution;
V) adding to the resulting copper-pregnant aqueous strip solution a mist-suppressing quantity of at least one alkoxylated compound of claim 1; and
VI) electrowinning the copper from the copper-pregnant aqueous strip solution obtained in step V).

47. The method of claim 46 wherein in step V) the mist-suppressing quantity is in range of from about 2 to about 100 ppm.

48. The method of claim 47 wherein said quantity is in the range of from about 2 to about 30 ppm.

49. The method of claim 47 wherein said quantity is in the range of from about 5 to about 25 ppm.

50. The method of claim 45 wherein the at least one alkoxylated compound of claim 1 is an alkoxylated triethanolamine.

51. The method of claim 46 wherein in step I) the copper-pregnant acid leach solution is a sulfuric acid leach solution having a pH in the range of from about 0.9 to about 2.0.

* * * * *